United States Patent
Zorovich

[11] 4,024,642
[45] May 24, 1977

[54] DENTAL APPLIANCE
[75] Inventor: Dan Zorovich, Allentown, N.J.
[73] Assignee: Johnson & Johnson, New Brunswick, N.J.
[22] Filed: Aug. 26, 1975
[21] Appl. No.: 607,861
[52] U.S. Cl. ............................................... 32/33
[51] Int. Cl.² ...................................... A61C 17/04
[58] Field of Search ......................................... 32/33
[56] References Cited
UNITED STATES PATENTS

| | | | |
|---|---|---|---|
| 1,986,751 | 1/1935 | Robinson | 32/33 |
| 3,090,122 | 5/1963 | Erickson | 32/33 |
| 3,148,449 | 9/1964 | Van Lanigan | 32/33 |
| 3,426,430 | 2/1969 | Newman | 32/33 |
| 3,631,598 | 1/1972 | Lussier | 32/33 |
| 3,777,756 | 12/1973 | Lohr | 32/33 |

Primary Examiner—Robert Peshock
Attorney, Agent, or Firm—Geoffrey G. Dellenbaugh

[57] ABSTRACT

A dental appliance for removal of liquid from the mouth and for containment of solid debris which comprises a flat, flexible, generally hour glass-shaped shield attached to a bite block on one end. A suction tube for fluid removal connects with a system of suction channels within the shield terminating in apertures along only the edge of the shield. The appliance is placed in the mouth so that the narrow central portion of the shield is over the gum behind the subject lower tooth, the portion adjacent the bite block is on the lingual side thereof, the portion remote from the bite block is on the buccal side thereof, and the edge containing the suction apertures is lowermost.

10 Claims, 2 Drawing Figures

U.S. Patent     May 24, 1977     4,024,642
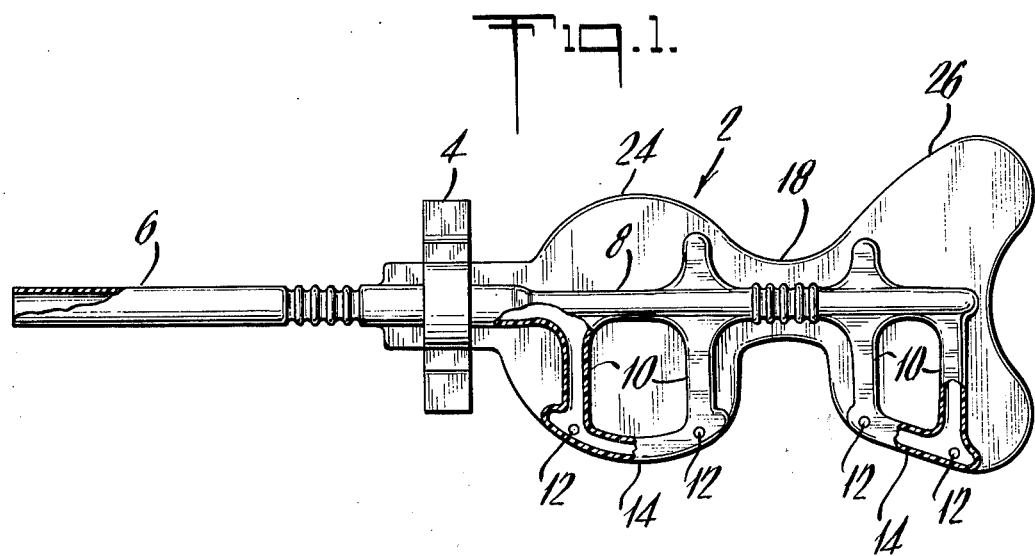
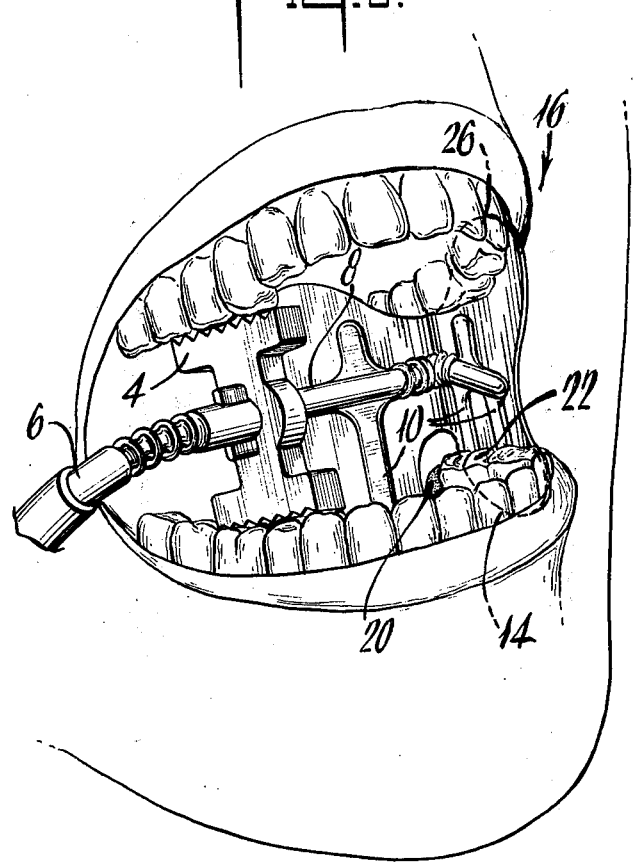

DENTAL APPLIANCE

BACKGROUND OF THE INVENTION

The problems relating to the removal of liquid from the mouth during dentistry are well known. Not only does saliva collect in the mouth during a dental operation, but modern, high-speed drills use water as a cooling medium for the tooth surface, thus increasing the amount of liquid in the mouth. It is desirable that such liquid be removed from the mouth during the dental operation, and to this end a number of devices designed to remove said liquid are known. See, for example, U.S. Pat. Nos. 2,937,455 and 3,090,122, both to Erickson. These prior art devices are of greatest use in the reclining patient and are intended to cover the throat opening and to remove liquid trapped in a central depressed area of the device.

These devices, however, have the disadvantage of being expensive to manufacture and therefore must be reused by the dentist, with all the difficulties attending such reuse. Thus, the device must be sterilized between uses, must be maintained in a sterile condition until use, and must be kept in a sufficiently large inventory to allow time for such sterilization.

Moreover, these prior art devices are generally of bulky construction and are uncomfortable in use, thereby irritating the patient during their use.

In addition, many of the prior art devices are limited in their application and can be used on only one side of the mouth. Therefore, it is necessary to keep twice as many of these prior art devices on hand as would otherwise be necessary.

A further disadvantage of these prior art devices is that they do not generally allow isolation of the buccal side of the teeth, and additional devices, such as cotton rolls, must be used.

SUMMARY OF THE INVENTION

It is an object of the present invention to provide a dental appliance for removal of liquid from the mouth which is sufficiently inexpensive so that it may be discarded after use. It is another object to provide such an appliance which can be used interchangeable on either side of the mouth. It is a further object to provide such an appliance which is less bulky and more convenient to use than those of the prior art. It is a still further object to provide such an appliance which allows isolation of a portion of the upper or lower jaw from both buccal and lingual secretions. These and other objects will become apparent from the following description taken in connection with the accompanying drawings.

The appliance of the invention comprises a relatively thin, flexible, generally hour-glass shaped shield member having a bite blocked attached to one end. Within said shield member is a system of suction channels terminating in apertures along only the edge of said shield member, which system connects to a drain channel having egress through a hole in the bite block. A suction tube connects with said drain channel for removal of the liquid therefrom.

The dental appliance of the invention will be understood more easly by reference to the accompanying drawings, in which:

FIG. 1 is a plan view with portions cut away of a preferred embodiment of the dental appliance of the invention;

FIG. 2 is a perspective view of the open mouth of a patient showing the appliance of FIG. 1 in place therein.

DETAILED DESCRIPTION OF THE FIGURES

Referring to FIGS. 1 and 2, a preferred embodiment of the dental appliance of the invention comprises a shield member 2 having a generally hour-glass shape attached to a bite block 4. Suction tube 6 connects with drain channel 8 of system 10 of suction channels terminating in apertures 12 along lower edge 14 of said shield member. Bite block 4 may be slideably moveable along suction tube 6. The appliance is placed in the mouth 16 so that the narrow central portion 18 of said shield member is placed over the gum 20 behind the subject tooth 22, wider terminal portion 24 adjacent the bite block is on the lingual side of said tooth, wider terminal portion 26 remote from the bite block is on the buccal side of said tooth, and lower edge 14 containing the suction apertures 12 is lowermost. Terminal portion 26 is preferably forked as shown in the figures to conform to mouth configuration and to better hold the appliance in position.

When the dental appliance of the invention is placed in the mouth as illustrated in FIG. 2, the subject tooth is isolated from both buccal and lingual secretions so that it is maintained in a dry state during the operation. While the appliance of the invention is not limited to such use, the preferred use thereof is during a filling or surfacing operation rather than during drilling. During these surfacing operations it is extremely important that the tooth surface be dry to assure good contact between the tooth surface and the surfacing material. It should be understood, however, that the dental appliance of the invention may also be used during drilling or excavation of a tooth, in which procedure the suction channels would serve to remove not only saliva but also cooling water from the drill and the shield would serve to contain solid debris produced by the drilling process.

The shield member of the appliance of the invention should be constructed of a material having sufficient stiffness to constrain the tongue and cheek while at the same time being sufficiently flexible to allow easy conformability of the appliance to the mouth. Suitable materials for this shield member should have a hardness in the range of about 85 to about 95 SHORE A and are, for example, ethyl vinyl acetate, low density polyethylene, polyvinyl chloride, thermoplastic elastomers such as that gold by Uniroyal Company under the trade name "TPR" and that sold by Shell Oil Company under the trade name "KRATON", and the like. The bite block should be constructed of a somewhat yielding material so that the patient may get a good grip thereon with his teeth; however, the material should be sufficiently rigid so that the patient may bite hard thereon without appreciably deforming it. Any of the above-listed shield member materials are suitable for the bite block.

The appliance of the invention has been illustrated by reference to a preferred embodiment, but such is only for purposes of illustration and not to limit the scope thereof.

What is claimed is:

1. A dental appliance for removal of liquid from the mouth and for containment of solid debris during dental work on a tooth which comprises:

A. a relatively thin, flexible shield member, said shield member having an upper edge and a lower edge, a narrow central portion adapted to be placed over the gum behind said tooth, a first wider terminal portion adapted to be placed on the lingual side of said tooth, and a second wider terminal portion adapted to be placed on the buccal side of said tooth;

B. a suction tube connecting with the end of said first wider terminal portion of said shield member;

C. a system of suction channels within said shield member and terminating in apertures along only said upper and lower edges of said shield member, said suction channels connecting to a drain channel having egress through said suction tube whereby liquid is removed from both lingual and buccal sides of said tooth; and D. a bite block carried on said suction tube, whereby the appliance is secured in the mouth.

2. A dental appliance as in claim 1 wherein said shield member is substantially hour-glass shaped.

3. A dental appliance as in claim 1 wherein said suction channel apertures are only in said wide terminal portions.

4. A dental appliance as in claim 1 wherein said second terminal portion is forked.

5. A dental appliance as in claim 1 wherein said shield member is made of ethyl vinyl acetate.

6. A dental appliance as in claim 1 wherein said bite block is attached to the end of said first wider terminal portion of said shield member.

7. A dental appliance as in claim 1 wherein said bite block has a hole therethrough, through which said suction tube passes.

8. A dental appliance as in claim 1 wherein said bite block is slideably moveable along said suction tube.

9. A dental appliance as in claim 1 wherein said shield member has a hardness in the range of about 85 to about 95 SHORE A.

10. A dental appliance as in claim 1 wherein said apertures are along only said lower edge of said shield member.

* * * * *

UNITED STATES PATENT AND TRADEMARK OFFICE
CERTIFICATE OF CORRECTION

PATENT NO. : 4,024,642
DATED : May 24, 1977
INVENTOR(S) : Dan Zorovich

It is certified that error appears in the above–identified patent and that said Letters Patent are hereby corrected as shown below:

In Column 1, Line 56, "blocked" should read ---block---

In Column 2, Line 27, "during the operation" should read ---during the dental operation---

In Column 2, Line 51, "gold" should read ---sold---

Signed and Sealed this

Twenty-first Day of March 1978

[SEAL]

Attest:

RUTH C. MASON
Attesting Officer

LUTRELLE F. PARKER
Acting Commissioner of Patents and Trademarks